United States Patent
McGall et al.

(10) Patent No.: US 10,533,216 B2
(45) Date of Patent: Jan. 14, 2020

(54) OLIGONUCLEOTIDE PROBE INVERSION PROCESS FOR IN SITU SYNTHESIZED PROBE ARRAYS

(71) Applicant: CENTRILLION TECHNOLOGY HOLDINGS CORPORATION, Grand Cayman (KY)

(72) Inventors: Glenn McGall, Palo Alto, CA (US); Vijay Singh, Mountain View, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 195 days.

(21) Appl. No.: 15/305,213

(22) PCT Filed: May 22, 2015

(86) PCT No.: PCT/US2015/032227
§ 371 (c)(1),
(2) Date: Oct. 19, 2016

(87) PCT Pub. No.: WO2015/179790
PCT Pub. Date: Nov. 26, 2015

(65) Prior Publication Data
US 2017/0067095 A1 Mar. 9, 2017

Related U.S. Application Data

(60) Provisional application No. 62/002,760, filed on May 23, 2014.

(51) Int. Cl.
*C07H 21/00* (2006.01)
*C12Q 1/6837* (2018.01)
*C12Q 1/6834* (2018.01)
*C40B 50/18* (2006.01)

(52) U.S. Cl.
CPC ......... *C12Q 1/6837* (2013.01); *C12Q 1/6834* (2013.01); *C40B 50/18* (2013.01)

(58) Field of Classification Search
None
See application file for complete search history.

(56) References Cited

U.S. PATENT DOCUMENTS

| | | | |
|---|---|---|---|
| 5,242,974 A | 9/1993 | Holmes | |
| 5,959,098 A | 9/1999 | Goldberg et al. | |
| 6,077,608 A | 6/2000 | Barkac et al. | |
| 6,262,216 B1 | 7/2001 | McGall | |
| 6,835,827 B2 | 12/2004 | Vinayak et al. | |
| 8,105,821 B2 | 1/2012 | McGall et al. | |
| 9,328,382 B2 | 5/2016 | Drmanac et al. | |
| 2002/0051994 A1 | 5/2002 | Kwiatkowski et al. | |
| 2004/0152905 A1 | 8/2004 | Guzaev et al. | |
| 2007/0037175 A1 | 2/2007 | Leproust et al. | |
| 2008/0305964 A1 | 12/2008 | Bar-Ziv et al. | |
| 2010/0261181 A1 | 10/2010 | Agnew et al. | |
| 2011/0223585 A1 | 9/2011 | Gullberg et al. | |
| 2012/0035115 A1 | 2/2012 | Manoharan et al. | |
| 2012/0083417 A1 | 4/2012 | Zhou et al. | |
| 2013/0165350 A1 | 6/2013 | Kuimelis et al. | |
| 2013/0237459 A1 | 9/2013 | Rasmussen | |
| 2014/0186940 A1 | 7/2014 | Goel | |
| 2016/0046985 A1 | 2/2016 | Drmanac et al. | |
| 2016/0168632 A1 | 6/2016 | Edwards | |
| 2017/0022554 A1 | 1/2017 | Drmanac et al. | |

FOREIGN PATENT DOCUMENTS

| | | |
|---|---|---|
| CN | 102702010 A | 10/2012 |
| CN | 103502218 A | 1/2014 |
| WO | WO-9851698 A1 | 11/1998 |
| WO | WO-2011106460 A2 | 9/2011 |
| WO | WO-2012106546 A2 | 8/2012 |
| WO | WO-2011106460 A3 | 2/2013 |
| WO | WO-2012106546 A3 | 11/2013 |
| WO | WO-2015017759 A1 | 2/2015 |
| WO | WO-2015179790 A1 | 11/2015 |
| WO | WO-2017031278 A1 | 2/2017 |
| WO | WO-2018102660 | 6/2018 |

OTHER PUBLICATIONS

Angela et al. Organic Letters (2012), vol. 14, pp. 1804-1807.*
Beaucage S.L. Strategies in the preparation of DNA oligonucleotide arrays for diagnostic applications. Curr. Med. Chem. Aug. 2001; 8(10): 1213-44.
"Beier, M et al. Production by the quantitative photolithographic synthesis of individually quality checked DNA microarrays. Nucleic Acid Research, vol. 28, No. 4, 2000, e11, pp. 1-6;".
Brown T, et al. Solid-phase oligonucleotide synthesis. [Online] Southampton, UK, ATDBio. http://www.atdbio.com/content/17/Solid-phase-oligonucleotide-synthesis [Accessed Aug. 9, 2016].
Chow B.Y., et al. Photoelectrochemical synthesis of DNA microarrays. Proc Natl Acad Sci USA 2009, 106, 15219-24.
Co-pending U.S. Appl. No. 15/240,114, filed Aug. 18, 2016.
Lindroos, et al. Minisequencing on oligonucleotide microarrays: comparison of immobilisation chemistries. Nucleic Acids Res. Jul. 1, 2001; 29(13): e69.
Forman, et al., Molecular Modeling of Nucleic Acids, Chapter 13, p. 221, American Chemical Society (1998).
Hughes T. R., et al. Expression profiling using microarrays fabricated by an ink-jet oligonucleotide synthesizer. Nature Biotechnol 2001, 19, 342-7.
International search report and written opinion dated Aug. 19, 2015 for PCT Application No. PCT/US2015/032227.
"International search report with written opinion dated Oct. 31, 2016 for PCT/US16/47488".
Kool Eric T., Versatile 5'—Functionalization of Oligonucleotides on Solid Support: Amines, Azides, Thiols, and Thioethers via Phosphorus Chemistry. J Org. Chem. 2004, 69, 2404-2410.

(Continued)

*Primary Examiner* — Patrick T Lewis
(74) *Attorney, Agent, or Firm* — Wilson Sonsini Goodrich & Rosati, LLP

(57) ABSTRACT

The present disclosure relates to processes for inverting oligonucleotide probes in an in situ synthesized array. These processes can be used to reverse the orientation of probes with respect to the substrate from 3'-bound to 5'-bound. These processes can also be used to reduce or eliminate the presence of truncated probe sequences from an in situ synthesized array.

15 Claims, 20 Drawing Sheets

(56) References Cited

OTHER PUBLICATIONS

Kumar, et al. Template-Directed Oligonucleotide Strand Ligation, Covalent Intramolecular DNA Circularization and Catenation Using Click Chemistry. JACS, 2007, 129(21), 6859.

Lausted C., et al. POSaM: a fast, flexible, open-source, inkjet oligonucleotide synthesizer and microarrayer.Genome Biol 2004, 5, R58.

"Markiewicz, WT et al. A new method of synthesis of fluorescently labelled oligonucleotides and their application in DNA sequencing. Nucleic Acids Research, vol. 25, No. 18, 1997, pp. 3672-3680".

Marshall et al. DNA chips: an array of possibilities. Nat. Biotechnol. Jan. 1998; 16:27-31.

Maurer, et al. Electrochemically Generated Acid and Its Containment to 100 Micron Reaction Areas for the Production of DNA Microarrays. PLoS ONE. 2006; 1(1): e34.

McGall, et al. Light-directed synthesis of high-density oligonucleotide arrays using semiconductor photoresists. Proc Natl Acad Sci USA 1996; 93:13555-60.

McGall G., et al. The efficiency of light-directed synthesis of DNA arrays on glass substrates J. Am. Chem. Soc. 119:5081-5090 (1997).

McGall G. H., et al. Photolithographic synthesis of arrays. In Methods in Molecular Biology: DNA Arrays, Methods and Protocols; J.B. Rampal, Ed.; Humana Press: Torowa, NJ, 2001; vol. 170, 71-101.

Pawloski A.R., et al. Photolithographic synthesis of high-density DNA probe arrays : Challenges and opportunities. J Vac Sci Technol B 2007, 25, 2537-46.

Pease A.C., et al. Light-generated oligonucleotide arrays for rapid DNA sequence analysis. Proc Natl Acad Sci USA 1994, 91, 5022-6.

Schena M. DNA Microarrays: A Practical Approach (Practical Approach Series). Oxford University Press. 1st edition.

Shelbourne et al. Fast copper-free click DNA ligation by the ring-strain promoted alkyne-azide cycloaddition reaction. Chem. Commun., 2011, 47:6257-6259.

Singh-Gasson S., et al. Maskless fabrication of light-directed oligonucleotide microarrays using a digial micromirror array.Nature Biotechnol 1999, 17, 974-8.

Spitale RC, et al. Structural imprints in vivo decode RNA regulatory mechanisms. Nature, 2015, 519(7544):486-90.

Gunderson, et al. A genome-wide scalable SNP genotyping assay using microarray technology. Nat Genet 37:549-554.

Glen Research Corporation, Catalog 2011.

PCT/US2016/047488 International Preliminary Report on Patentability dated Mar. 1, 2018.

PCT/US2017/064169 International Search Report and Written Opinion dated Mar. 7, 2018.

Extended European Search Report and Search Opinion dated Oct. 19, 2017 for European Patent Application No. 15796731.6.

Kwiatkowski, et al., Inversion of in situ synthesized oligonucleotides; improved reagents for hybridization and primer extension in DNA microarrays, Nucleic Acids Research, Information Retrieval Ltd, Jan. 1, 1999, 27(24):4710-14.

CN2015800273478 Office Action dated May 23, 2018 (w/ English translation).

EP15796731.6 Extended Search Report dated Oct. 19, 2017.

EP16184815.5 Extended Search Report dated Jan. 2, 2017.

Horn et al. Chemical synthesis and characterization of branched oligodeoxyribonucleotides (bDNA) for use as signal amplifiers in nucleic acid quantification assays. Nucleic Acids Research 25(23):4842-4849 (Jan. 1, 1997).

PCT/US2015/032227 International Preliminary Report on Patentability dated Nov. 29, 2016.

PCT/US2016/047488 International Preliminary Report on Patentability dated Feb. 20, 2018.

U.S. Appl. No. 15/240,114 Office Action dated Jun. 15, 2018.

\* cited by examiner

OLIGONUCLEOTIDE PROBE INVERSION PROCESS FOR IN SITU SYNTHESIZED PROBE ARRAYS

CROSS-REFERENCE

This application claims the benefit of U.S. Provisional Application No. 62/002,760, filed May 23, 2014, which application is incorporated herein by reference.

BACKGROUND

The synthesis of oligonucleotide probes on in situ synthesized arrays, such as by photolithography, can result in a population of incomplete or "truncated" probe sequences which accompany the probe sequences synthesized at the full desired or intended length ("full-length" probe sequences). The presence of truncated probe sequences can have a detrimental effect on array performance, especially in assays requiring enzymatically addressing the free probe terminus (e.g., polymerase extension reactions, ligation reactions).

In contrast, oligonucleotide probes immobilized on bead arrays (e.g., Illumina) and other spotted arrays may be attached to their substrates via an amine or other functional group synthetically attached to the 5'-end of the probe. In this way, only full-length sequences may be immobilized, and truncations or other defects associated with an exposed free 3'-end may be reduced or virtually eliminated.

SUMMARY OF THE INVENTION

It may be desirable to selectively remove truncated probe sequences post-synthesis from among the probes on in situ synthesized arrays, such as those fabricated with photolithography. The present disclosure provides processes for accomplishing this selective removal of truncated sequences, while simultaneously inverting the orientation of the probe sequence such that probe sequences synthesized from the 3'-end can be converted to probe sequences attached to the substrate via their 5'-end.

In particular, this disclosure includes probe inversion processes for in situ synthesized arrays which can use universal linkers and commercially available building blocks and reagents. These can include incorporation of a universal cleavable linker phosphoramidite for use in releasing free 3'-OH termini, incorporation of branched linkers with orthogonally addressable functional groups for oligonucleotide synthesis and post-synthesis circularization, more efficient crosslinking chemistries for circularization steps utilizing commercially available reagents, and other improvements. Previous processes attempting probe inversion on in situ synthesized arrays involved a large number of special linkers, building blocks and reagents, which can make it impractical to use for large scale manufacturing of in situ synthesized arrays.

An aspect of the present disclosure provides a method, comprising: (a) providing a substrate; (b) coupling a branched linker to said substrate, wherein said branched linker comprises (i) a first branch comprising a post-synthesis reactive group and (ii) a second branch; (c) coupling a cleavable linker to said second branch; (d) synthesizing an oligonucleotide on said cleavable linker in 3' to 5' orientation, said oligonucleotide comprising (i) a 3' end coupled to said second branch via said cleavable linker and (ii) a 5' end coupled to an OH group; (e) reacting said OH group to provide a circularization group coupled to said 5' end of said oligonucleotide; (f) circularizing said oligonucleotide by reacting said circularization group with said post-synthesis reactive group, thereby coupling said 5' end of said oligonucleotide to said first branch; and (g) cleaving said cleavable linker, thereby de-coupling said 3' end of said oligonucleotide from said second branch.

In some embodiments of aspects provided herein, said branched linker is coupled to said substrate via an OH group bound to said substrate. In some embodiments of aspects provided herein, said branched linker comprises the structure shown in FIG. 3A. In some embodiments of aspects provided herein, said branched linker comprises the structure shown in FIG. 3B. In some embodiments of aspects provided herein, said cleavable linker comprises the structure shown in FIG. 4A. In some embodiments of aspects provided herein, said cleavable linker comprises the structure shown in FIG. 4B. In some embodiments of aspects provided herein, said branched linker is coupled to said substrate via an OH group bound to said substrate. In some embodiments of aspects provided herein, said circularizing is conducted using phosphotriester or H-phosphonate chemistry. In some embodiments of aspects provided herein, said circularizing is conducted using carboxamide coupling. In some embodiments of aspects provided herein, said circularizing is conducted using Huisgen "click" chemistry. In some embodiments of aspects provided herein, said circularizing is conducted using thiophosphate-BrAc chemistry. In some embodiments of aspects provided herein, said circularizing is conducted using thiophosphate-haloalkane chemistry. In some embodiments of aspects provided herein, said cleaving comprises deprotection with $NH_4OH$. In some embodiments of aspects provided herein, said synthesizing comprises photolithography.

An aspect of the present disclosure provides a method, comprising: (a) providing a substrate comprising a plurality of sites; (b) coupling a branched linker to each of said plurality sites, wherein said branched linker comprises (i) a first branch comprising a post-synthesis reactive group and (ii) a second branch; (c) coupling a cleavable linker to said second branch of said branched linker on each of said sites; (d) synthesizing oligonucleotide probes in 3' to 5' orientation on said cleavable linker on each of said sites, thereby producing a (i) a full-length oligonucleotide coupled at a 3' end to said cleavable linker of a first site and coupled at a 5' end to an OH group, wherein said full-length oligonucleotide comprises a target number of nucleotides, and (ii) a truncated oligonucleotide coupled at a 3' end to said cleavable linker of a second site and lacking an OH group at a 5' end, wherein said truncated oligonucleotide comprises fewer than said target number of nucleotides, and; (e) reacting said OH group coupled to said 5' end of said full-length oligonucleotide to provide a circularization group coupled to said 5' end of said full-length oligonucleotide; (f) circularizing said full-length oligonucleotide by reacting said circularization group with said post-synthesis reactive group of said branched linker of said first site, thereby coupling said 5' end of said full-length oligonucleotide to said first branch of said branched linker of said first site; and (g) cleaving said cleavable linker of each of said plurality sites, thereby (i) de-coupling said 3' end of said full-length oligonucleotide from said second branch of said branched linker of said first site, and (ii) releasing said truncated oligonucleotide from said second site.

In some embodiments of aspects provided herein, said branched linker is coupled to said substrate via an OH group bound to said substrate. In some embodiments of aspects provided herein, said branched linker comprises the structure shown in FIG. 3A. In some embodiments of aspects provided herein, said branched linker comprises the structure shown in FIG. 3B. In some embodiments of aspects provided herein, said cleavable linker comprises the structure shown in FIG. 4A. In some embodiments of aspects provided herein, said cleavable linker comprises the structure shown in FIG. 4B. In some embodiments of aspects provided herein, said branched linker is coupled to said substrate via an OH group bound to said substrate. In some embodiments of aspects provided herein, said circularizing is conducted using phosphotriester or H-phosphonate chemistry. In some embodiments of aspects provided herein, said circularizing is conducted using carboxamide coupling. In some embodiments of aspects provided herein, said circularizing is conducted using Huisgen "click" chemistry. In some embodiments of aspects provided herein, said circularizing is conducted using thiophosphate-BrAc chemistry. In some embodiments of aspects provided herein, said circularizing is conducted using thiophosphate-haloalkane chemistry. In some embodiments of aspects provided herein, said cleaving comprises deprotection with $NH_4OH$. In some embodiments of aspects provided herein, said synthesizing comprises photolithography. In some embodiments of aspects provided herein, said cleaving releases at least 50% of oligonucleotides that comprise fewer than said target number of nucleotides from said plurality of sites. In some embodiments of aspects provided herein, said cleaving releases at least 70% of oligonucleotides that comprise fewer than said target number of nucleotides from said plurality of sites. In some embodiments of aspects provided herein, said cleaving releases at least 90% of oligonucleotides that comprise fewer than said target number of nucleotides from said plurality of sites.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present disclosure provides processes for the circularization of in situ synthesized oligonucleotide probes. The processes disclosed herein can also reduce or eliminate truncated oligonucleotide probes, which do not contain the full synthesized oligonucleotide sequence, while preserving full-length oligonucleotide probes, which do contain the full synthesized oligonucleotide sequence.

The term "oligonucleotide" can refer to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "about" as used herein refers to +/−10%, 9%, 8%, 7%, 6%, 5%, 4%, 3%, 2%, or 1% of the designated amount.

Figure 1:
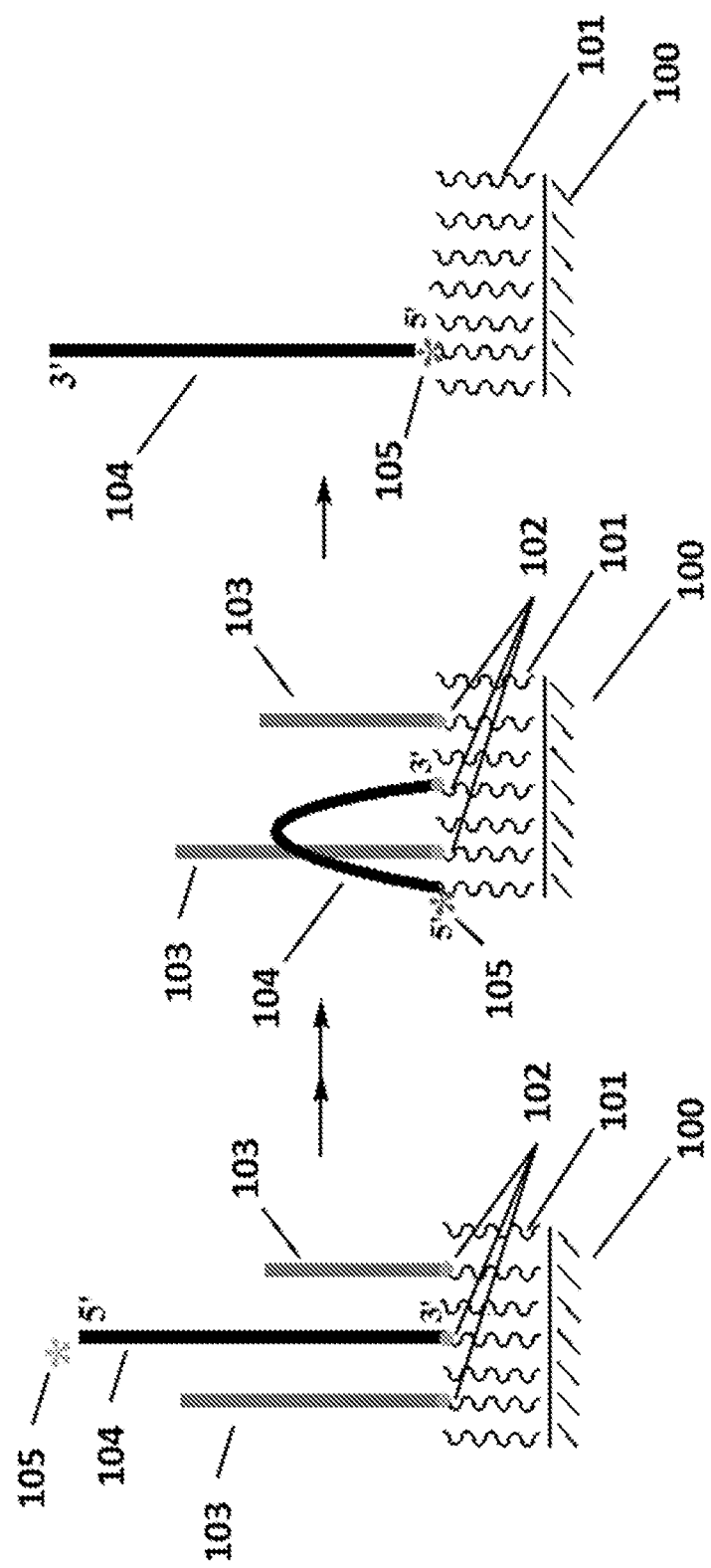
FIG. 1 shows an exemplary schematic of a probe inversion process.

FIG. 1 shows a schematic of an oligonucleotide probe inversion process which inverts full-length oligonucleotide probes from a 3'-5' orientation relative to the synthesis substrate to a 5'-3' orientation relative to the synthesis substrate, while also removing truncated oligonucleotide probes. A synthesis substrate 100 comprising active surface groups 101 is provided. Linkers 102 are coupled to the active surface groups, and oligonucleotide synthesis is conducted in situ, producing truncated 103 and full-length 104 oligonucleotide probes in 3'-5' orientation. A circularizing group 105 is provided to the 5' of only the full-length oligonucleotide probes. Then, the circularizing group is circularized to a linker, coupling the 5' end of the full-length oligonucleotide probes to the substrate. Finally, the linkers at the 3' ends of the synthesized oligonucleotides are cleaved, releasing the truncated oligonucleotide probes and leaving the full-length oligonucleotide probes coupled to the substrate at only the 5' end.

Figure 2A:
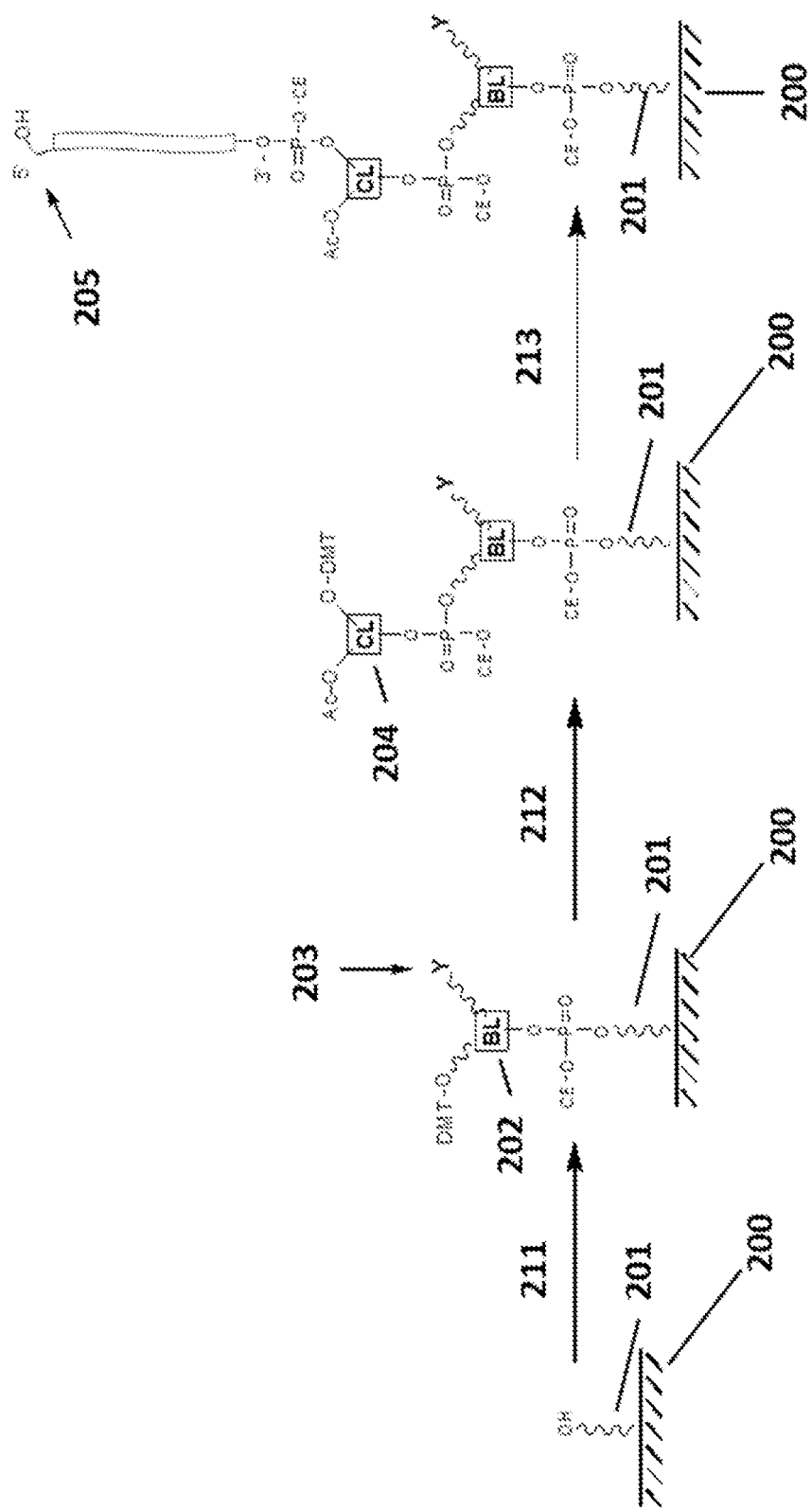
FIG. 2A shows an exemplary schematic of a first part of a probe inversion process.
Figure 2B:
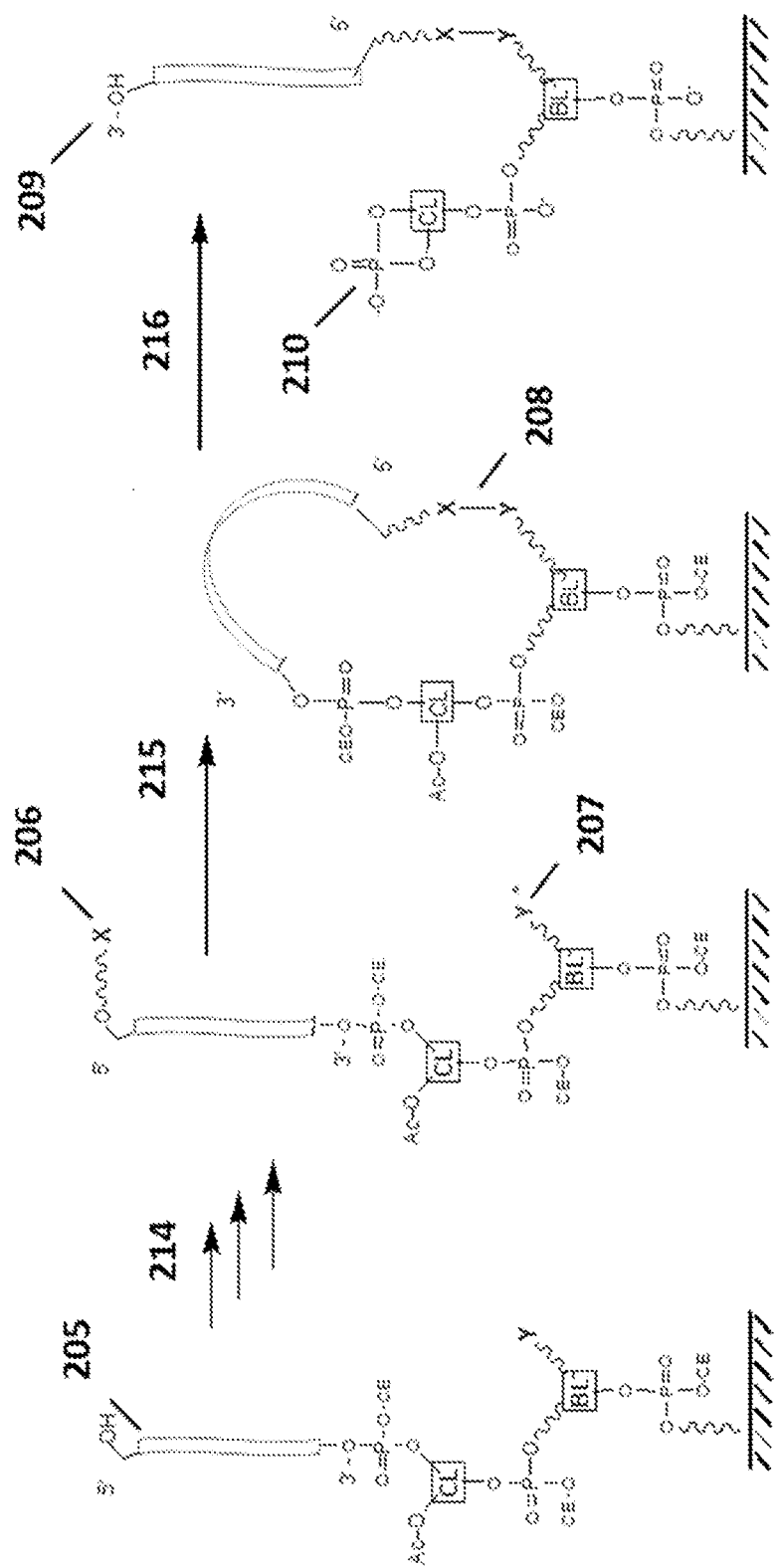
FIG. 2B shows an exemplary schematic of a second part of a probe inversion process.
Figure 3B:
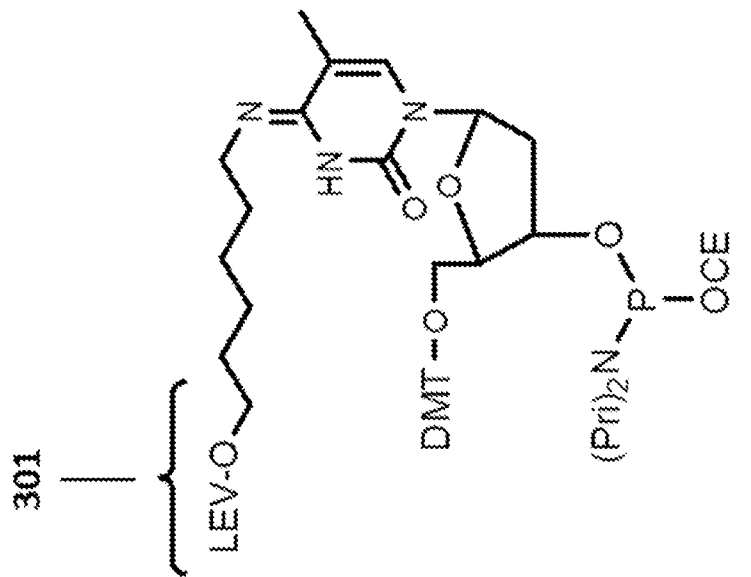
FIG. 3B shows an exemplary formula for a branching linker.
Figure 3A:
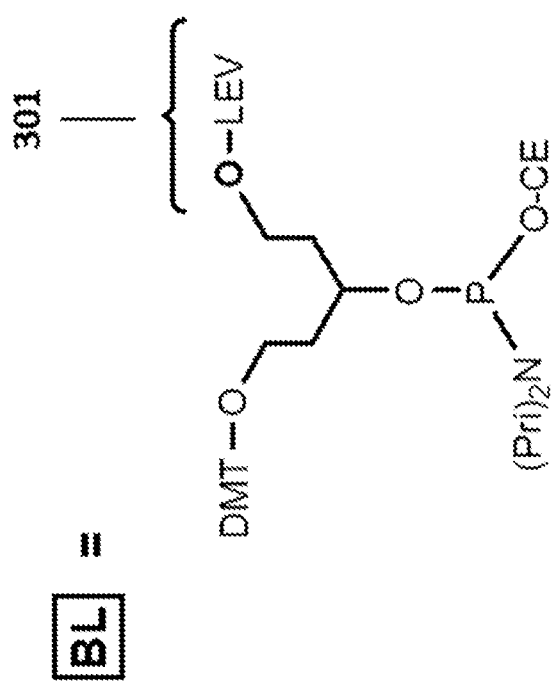
FIG. 3A shows an exemplary formula for a branching linker.
Figure 4B:
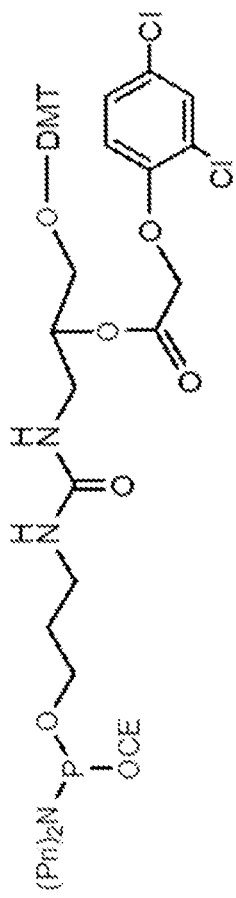
FIG. 4B shows an exemplary formula for a cleavable linker.
Figure 4A:
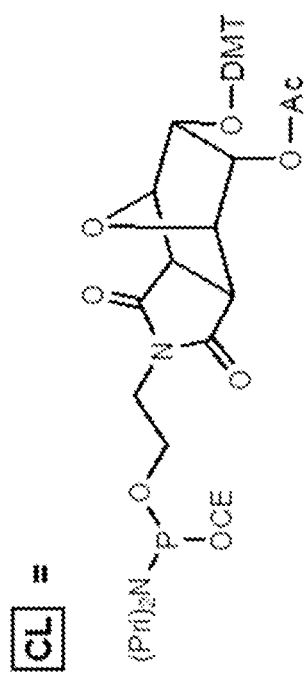
FIG. 4A shows an exemplary formula for a cleavable linker.

FIG. 2A and FIG. 2B show an exemplary schematic of probe inversion process chemistry. For example, beginning in FIG. 2A, a synthesis substrate 200 is provided, with active surface groups 201 comprising OH groups. The active surface group is reacted 211 to couple a branching linker amidite (BL) 202, comprising a post-synthesis reactive group 203, to the substrate. Branching linker amidites can be added to the synthesis substrate using standard DNA synthesis protocols. Exemplary branching linker amidites are shown in FIG. 3A and FIG. 3B. The branching linker amidite is reacted 212 to couple a cleavable linker amidite (CL) 204 to the branching linker. Cleavable linkers can be added to the synthesis substrate using standard DNA synthesis protocols. Exemplary cleavable linker amidites are shown in FIG. 4A and FIG. 4B. Oligonucleotide synthesis is conducted 213 in situ in the standard 3' to 5' direction, producing oligonucleotide probes coupled to the cleavable linkers. Full-length oligonucleotide probes 205 have 5' OH groups, while truncated oligonucleotide probes are capped. Continuing in FIG. 2B, OH groups at the 5' ends of full-length oligonucleotide probes are reacted 214 to add a circularizing group 206 to the 5' end of the probe, and the post-synthesis reactive group 207 on the branching linker is activated. The circularizing group and the post-synthesis reactive group are reacted 215 to produce a circularized full-length oligonucleotide probe 208. Truncated oligonucleotide probes remain uncircularized. Standard deprotection 216 (e.g., with $NH_4OH$) is used to deprotect the oligonucleotide probes and cleave the 3'-end cleavable linkers. This results in inverted full-length oligonucleotide probes 209, now coupled to the substrate at the 5' end. Cleaved cleavable linkers 210 remain, and truncated oligonucleotide probes are released from the substrate.

Figure 5A:
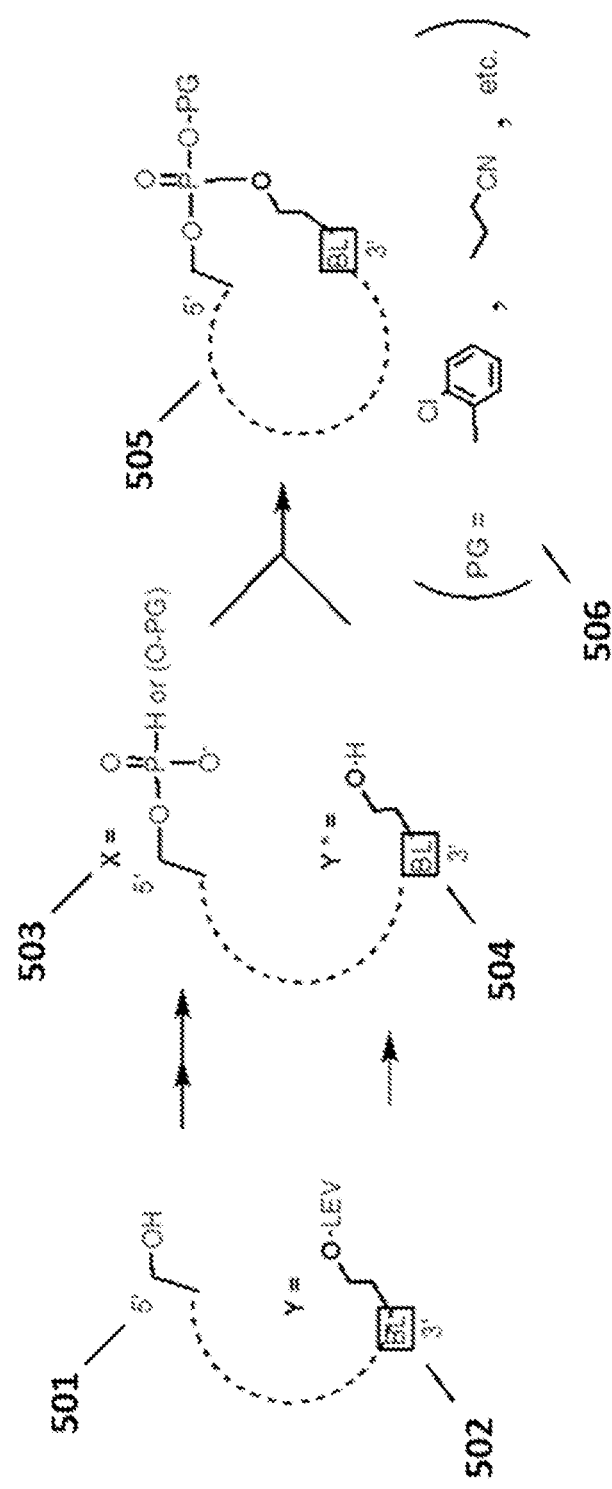
FIG. 5A shows an exemplary schematic of a circularization chemistry using phosphotriester or H-phosphonate chemistry.
Figure 5B:
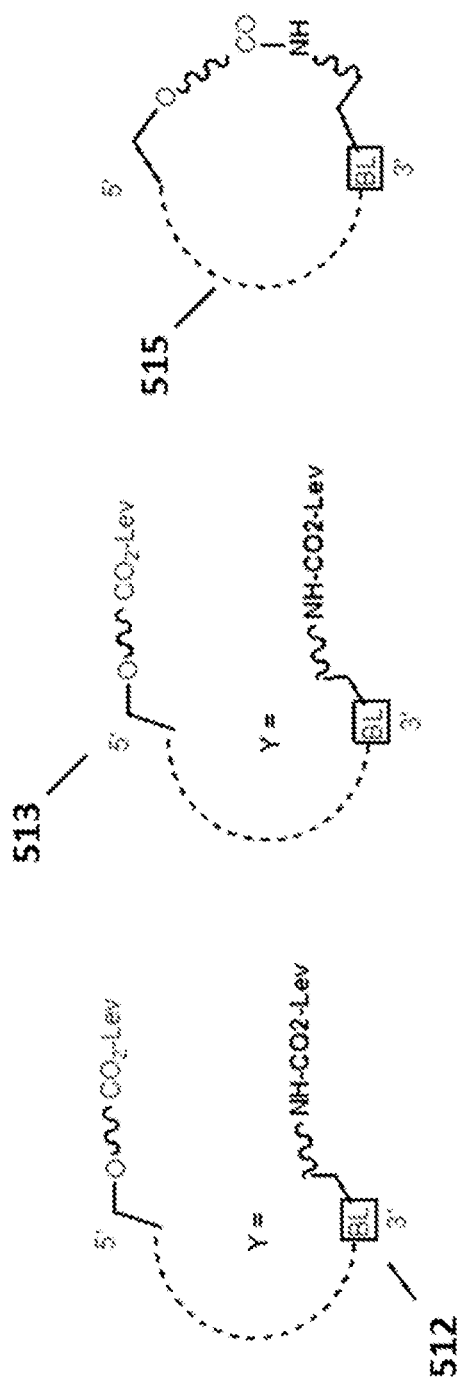
FIG. 5B shows an exemplary schematic of a circularization chemistry using carboxamide coupling.
Figure 5C:
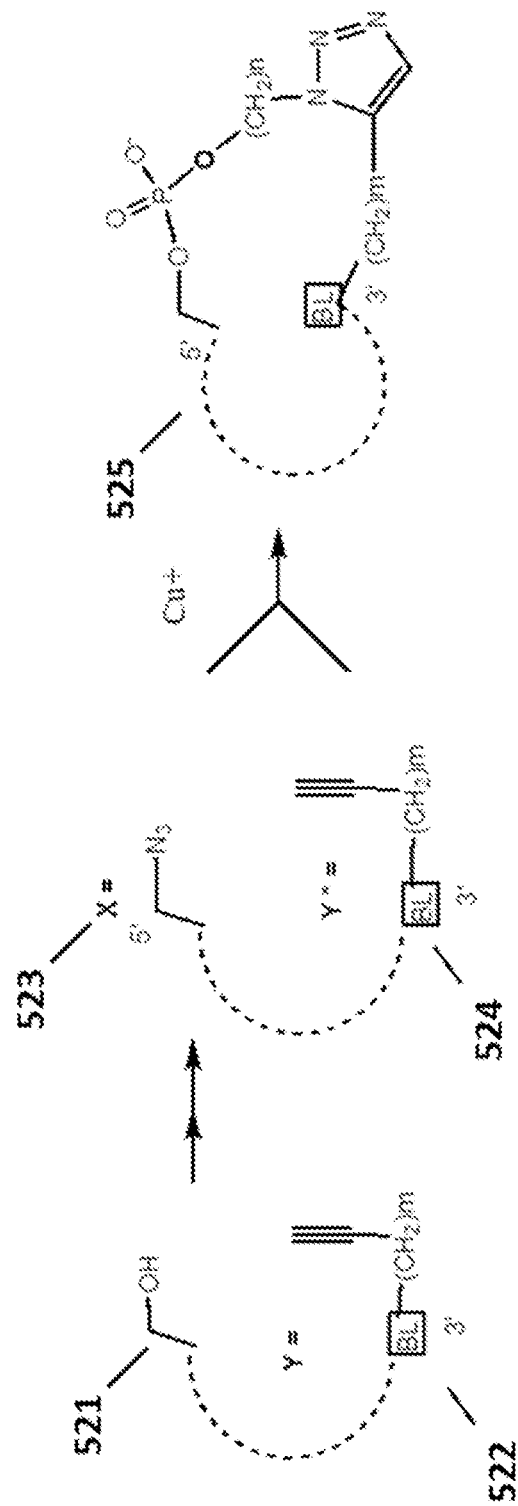
FIG. 5C shows an exemplary schematic of a circularization chemistry using Huisgen "click" chemistry.
Figure 5D:
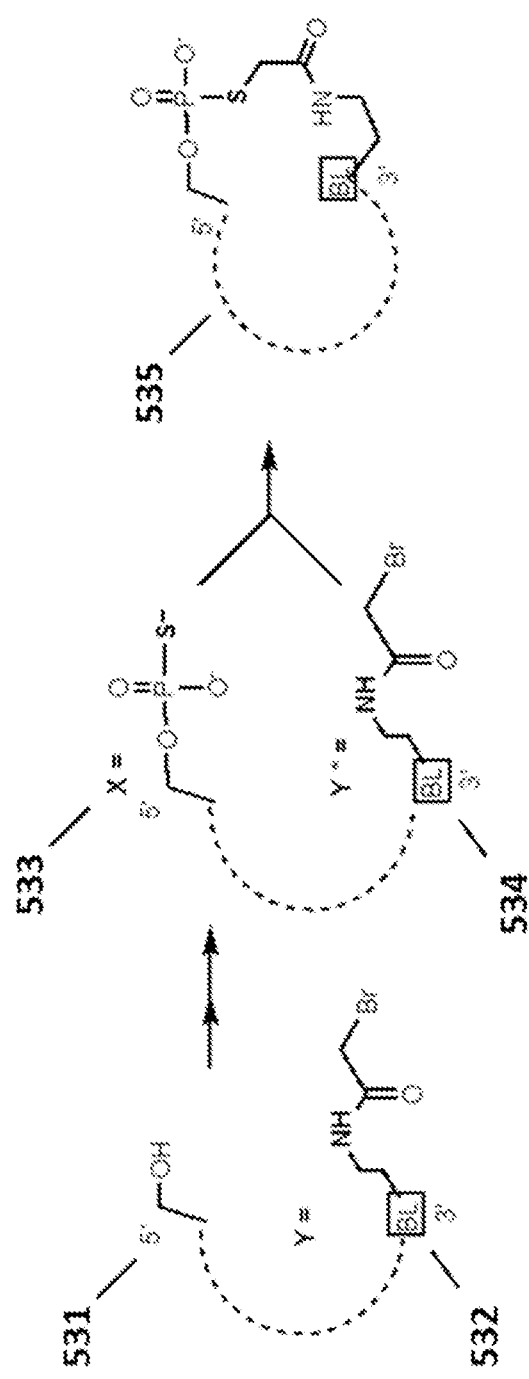
FIG. 5D shows an exemplary schematic of a circularization chemistry using thiophosphate-BrAc chemistry.
Figure 5E:
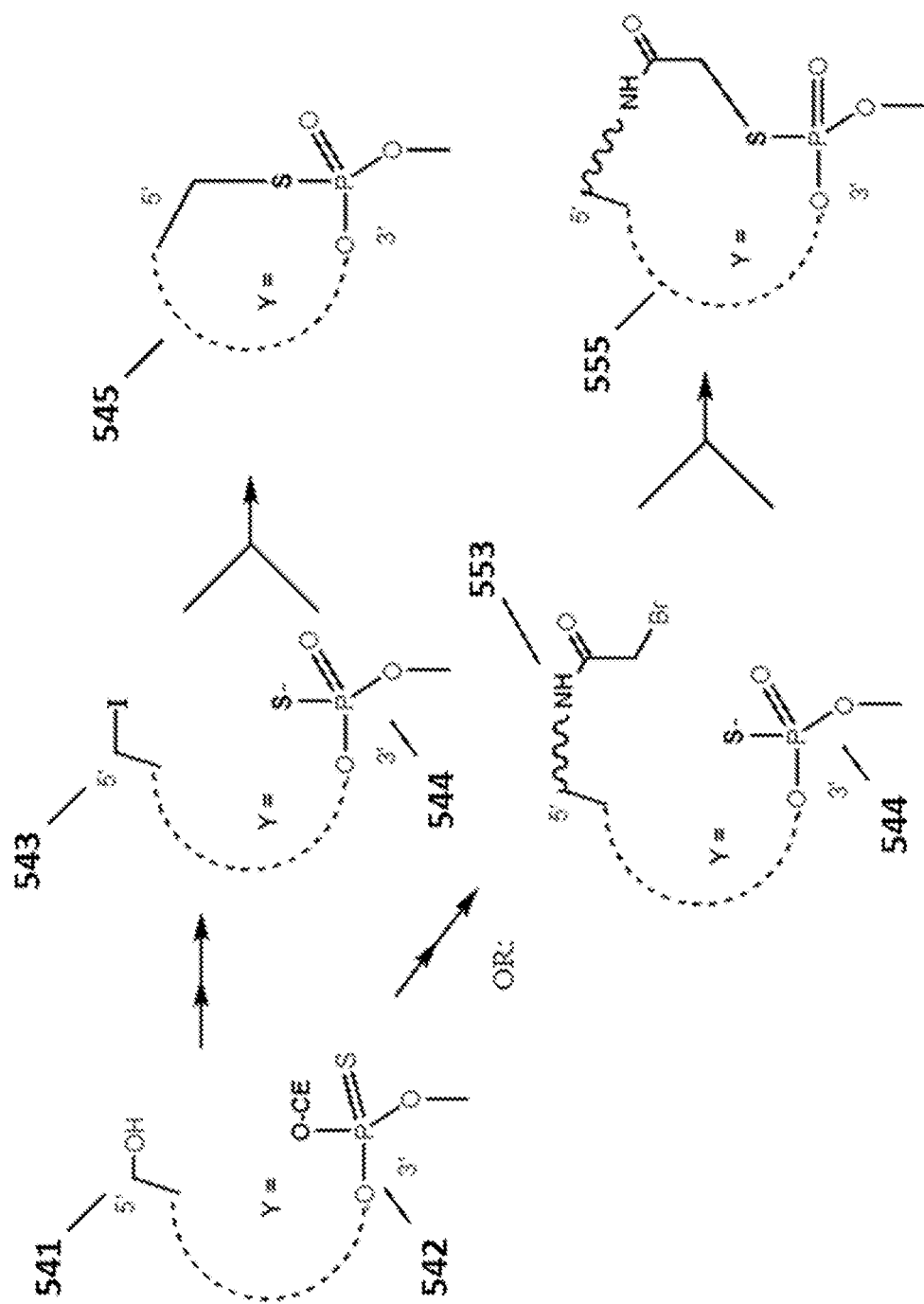
FIG. 5E shows an exemplary schematic of a circularization chemistry using thiophosphate-haloalkane chemistry.
Figure 6:
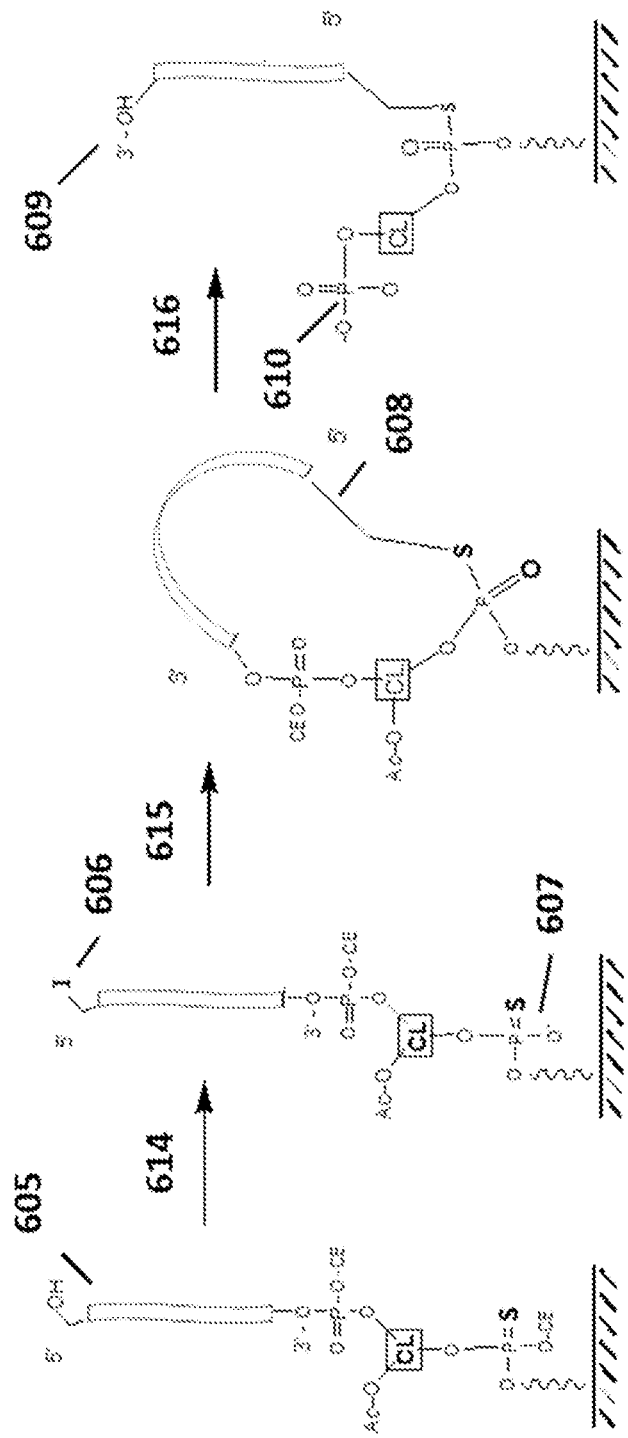
FIG. 6 shows an exemplary schematic of a second part of a probe inversion process using iodide and thiophosphate chemistry.

Various circularization chemistries can be employed with the processes described herein. Exemplary circularization chemistries are shown in FIG. 5A, FIG. 5B, FIG. 5C, FIG. 5D, and FIG. 5E. FIG. 5A shows an exemplary schematic of a circularization chemistry using phosphotriester or H-phosphonate chemistry. The OH group at the 5' end of a full-length oligonucleotide probe 501 and a post-synthesis reactive group 502 are provided as shown. A circularization group 503 as shown is coupled to the 5' end of the full-length oligonucleotide probe, and the post-synthesis reactive group is activated 504 as shown. The circularization group and the post-synthesis reactive group are circularized 505. Example groups useful for the PG group shown in 503 and 505 are shown in 506. FIG. 5B shows an exemplary schematic of a circularization chemistry using carboxamide coupling. The OH group at the 5' end of a full-length oligonucleotide probe and a post-synthesis reactive group 512 are provided. A circularization group 513 as shown is coupled to the 5' end of the full-length oligonucleotide probe. The circularization group and the post-synthesis reactive group are circularized 515. FIG. 5C shows an exemplary schematic of a circularization chemistry using Huisgen "click" chemistry. The OH group at the 5' end of a full-length oligonucleotide probe 521 and a post-synthesis reactive group 522 are provided as shown. A circularization group 523 as shown is coupled to the 5' end of the full-length oligonucleotide probe, and the post-synthesis reactive group is activated 524 as shown. The circularization group and the post-synthesis reactive group are circularized 525 with the use of Cu+. FIG. 5D shows an exemplary schematic of a circularization chemistry using thiophosphate-BrAc chemistry. The OH group at the 5' end of a full-length oligonucleotide probe 531 and a post-synthesis reactive group 532 are provided as shown. A circularization group 533 as shown is coupled to the 5' end of the full-length oligonucleotide probe, and the post-synthesis reactive group is activated 534 as shown. The circularization group and the post-synthesis reactive group are circularized 535. FIG. 5E shows two exemplary schematics of a circularization chemistry using thiophosphate-haloalkane chemistry. The OH group at the 5' end of a full-length oligonucleotide probe 541 and a post-synthesis reactive group 542 are provided as shown. A circularization group 543 or 553 as shown is coupled to the 5' end of the full-length oligonucleotide probe, and the post-synthesis reactive group is activated 544 as shown. The circularization group and the post-synthesis reactive group are circularized 545 or 555. Circularization can occur between a circularization group and a post-synthesis reactive group coupled to the same branched linker, or alternatively circularization can occur between a circularization group and a post-synthesis reactive group of a different nearby branched linker.

The synthesis substrate can comprise different forms or shapes, such as flow cells, sequencing flow cells, flow channels, microfluidic channels, capillary tubes, piezoelectric surfaces, wells, microwells, microwell arrays, microarrays, chips, wafers, surface arrays, non-magnetic beads, magnetic beads, ferromagnetic beads, paramagnetic beads, superparamagnetic beads, and polymer gels.

The synthesis substrate can comprise any suitable material, including but not limited to glass (e.g., controlled pore glass), silica, titanium oxide, aluminum oxide, indium tin oxide (ITO), silicon, polydimethylsiloxane (PDMS), polystyrene, polycyclicolefins, polymethylmethacrylate (PMMA), other plastic, titanium, or gold.

Substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

Releasing truncated probe sequences can increase the percentage of full-length sequences present in the array. In some cases, at least about 10%, 20%, 30%, 40%, 50%, 60%, 70%, 80%, 90%, 95%, 96%, 97%, 98%, 99%, 99.9%, 99.99%, or 99.999% of probes remaining bound to the array substrate following a probe inversion process are full-length sequences. In some cases, all or substantially all of the probes remaining bound to the array substrate following the probe inversion process are full-length sequences. In some cases, a probe inversion process can release at least about 10%, 20%, 30%, 40%, 50%, 60%, 70%, 80%, 90%, 95%, 96%, 97%, 98%, 99%, 99.9%, 99.99%, or 99.999% of truncated probes bound to the array substrate prior to the probe inversion process. In some cases, a probe inversion process can release all or substantially all of truncated probes bound to the array substrate prior to the probe inversion process.

EXAMPLE 1—OLIGONUCLEOTIDE PROBE SYNTHESIS AND INVERSION

Figure 7A:
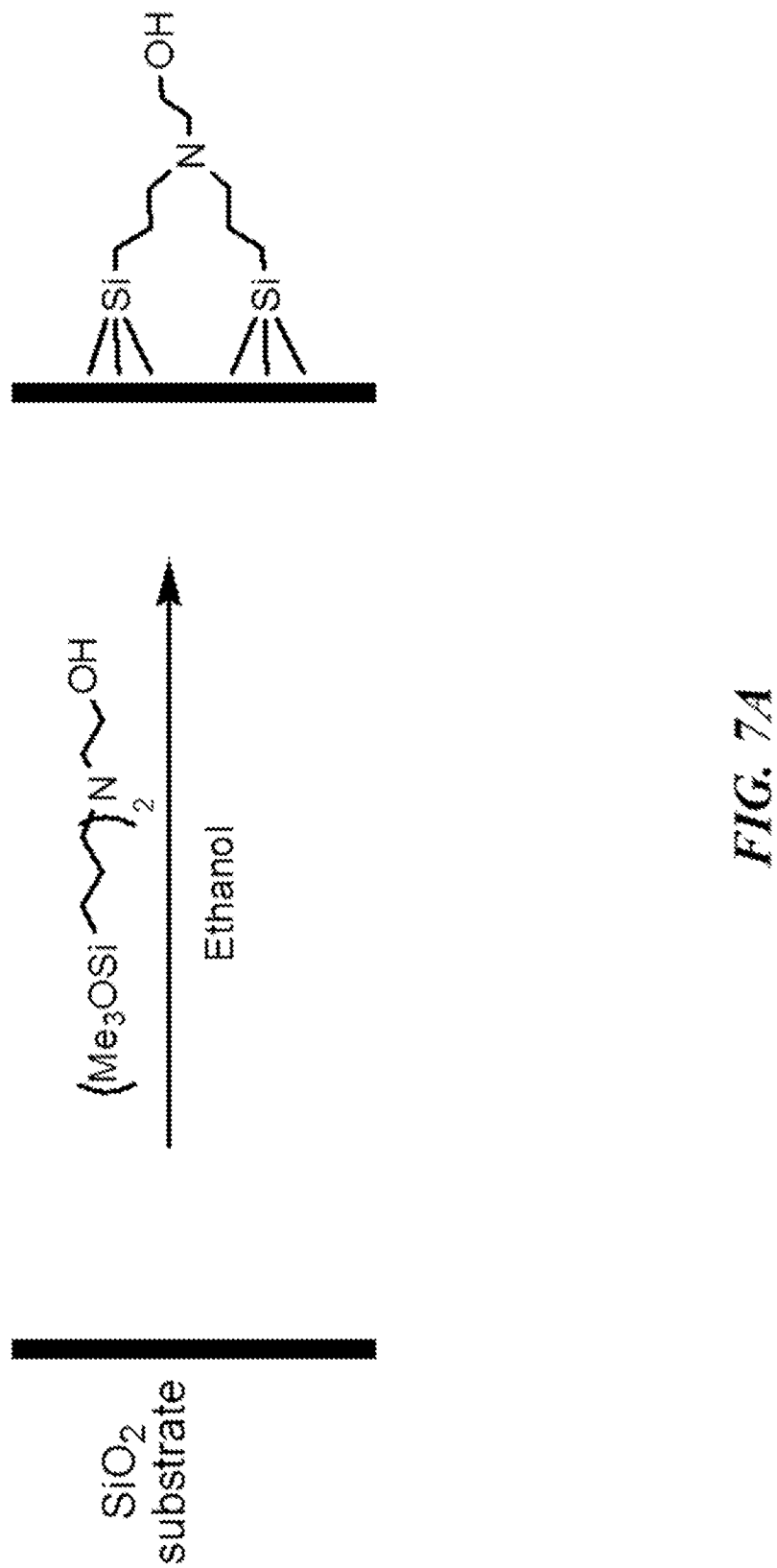
FIG. 7A shows an exemplary step of silanation of a $SiO_2$ substrate.

A suitable planar substrate, such as glass, silica, or silicon with a native oxide layer, is cleaned and "activated" with a surface layer of covalently bonded primary hydroxyl alkyl groups, which serve as the surface initiation sites for oligonucleotide synthesis. Any one of a variety of methods described previously, can be used (see, e.g., U.S. Pat. No. 5,959,098—"Substrate preparation process;" *J. Am. Chem. Soc.* 1997, 119(22), 5081—"The efficiency of light-directed synthesis of DNA arrays on glass substrates;" U.S. Pat. No. 6,262,216—"Functionalized silicon compounds and methods for their synthesis and use;" U.S. Pat. No. 8,105,821—"Silane mixtures;" U.S. Patent Pub. No. 2013165350 A1—"Surface Linkers for Array Synthesis"). In this example, the wafer is cleaned using a sulfuric acid—hydrogen peroxide mixture (e.g., Nanostrip™); water-rinsed, and dried. The substrate is then silanated by treatment with a solution comprising a mixture of N-(2-hydroxyethyl)-N,N,-bis(3-(trimethoxysilyl)propyl)amine and N-(2-cyanoethyl)-N,N,-bis(3-(trimethoxysilyl)propyl)amine (ratio 1:0 to 1:20, with a total silane concentration from 1-10% w/v) in ethanol for 1-8 hours (see, e.g., FIG. 7A). After silanation, the silanated substrate is rinsed with alcohol, water, and finally dried. The substrate is ready for array synthesis.

Figure 7B:
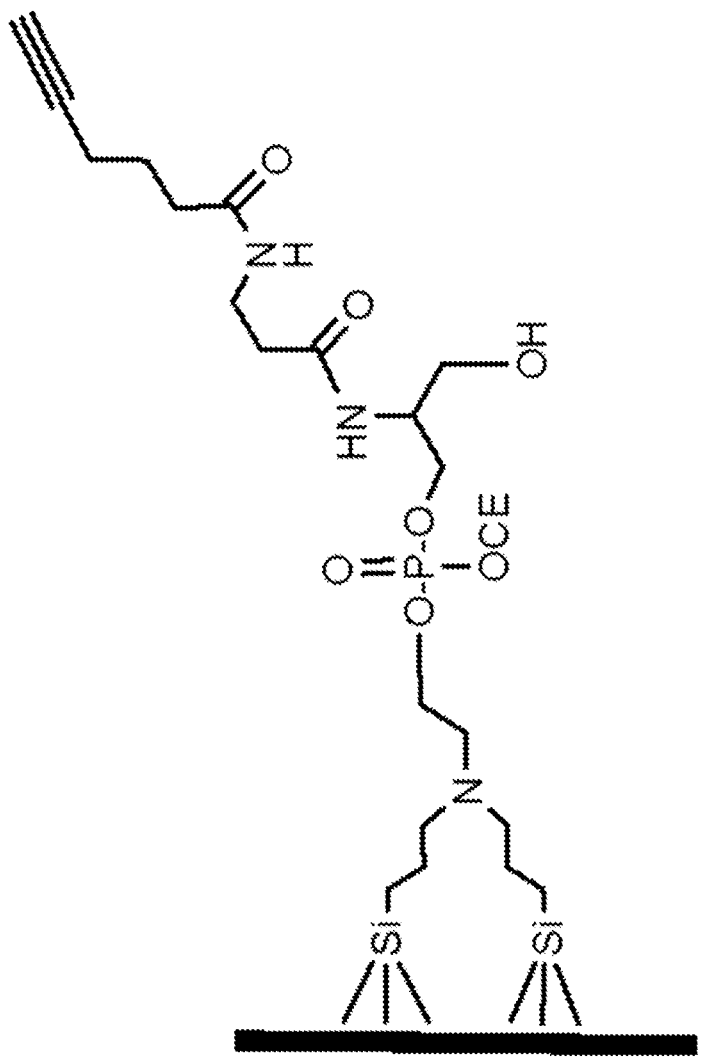
FIG. 7B shows an exemplary step of addition of a branched linker to a silanized substrate surface.

The active surface of the substrate is then placed on a sealed flowcell connected to an automated oligonucleotide synthesizer, and a branched linker with an alkyne sidechain (e.g., Alkyne-Modifier Serinol Phosphoramidite, Glen Research, P/N 10-1992) is added to the substrate surface, using standard solid-phase oligonucleotide synthesis protocols. This is followed by a deblocking step, using trichloroacetic acid, to expose the hydroxyl group of the linker for subsequent phosphoramidite additions (see, e.g., FIG. 7B). Optionally, one or more spacer phosphoramidites can be introduced prior to the attachment of the alkyne phosphoramidite. The alkyne side chain is the moiety which will later react to form a covalent bond with an azide group attached to the 5'-end of oligonucleotide probe sequences, once all of the full-length probe sequences are completed.

Figure 7C:
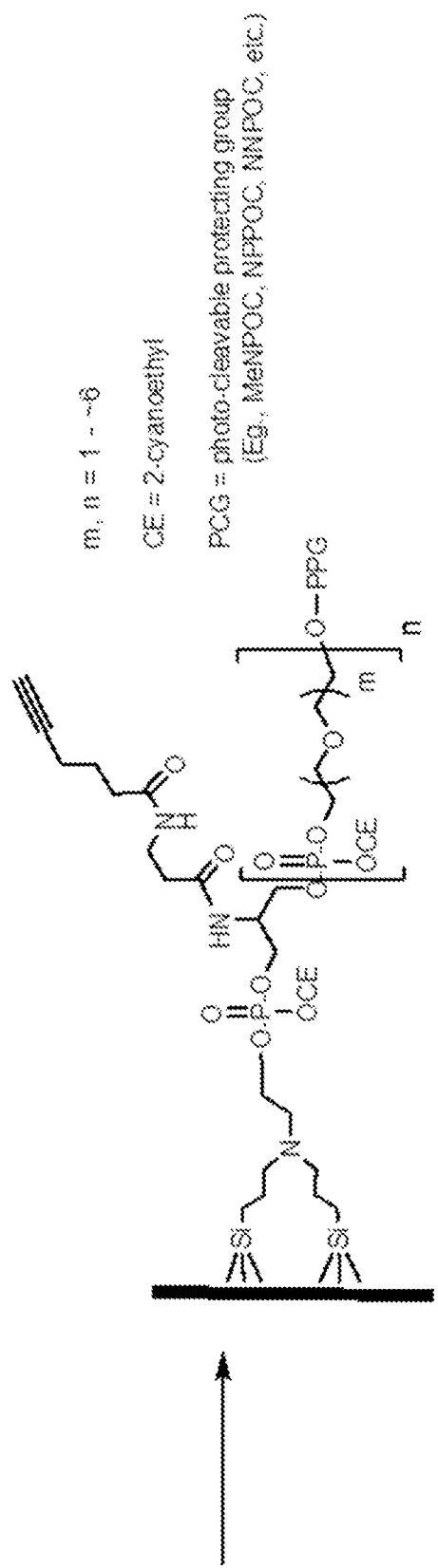
FIG. 7C shows an exemplary step of addition of linker phosphoramidites with consecutive cycles of light-activated oligonucleotide synthesis chemistry.

Next, one or more spacer phosphoramidites are added with consecutive cycles of light-activated oligonucleotide synthesis chemistry (see, e.g., FIG. 7C), the details of which have been described elsewhere (see, e.g., *J. Am. Chem. Soc.* 1997, 119(22), 5081—"The efficiency of light-directed synthesis of DNA arrays on glass substrates;" *Methods in Molecular Biology,* 2001, 170, 71, Rampal J B, ed.—"Photolithographic synthesis of high-density oligonucleotide arrays;" *Current Protocols in Nucleic Acid Chemistry* 2005, 12:12.5.1-12.5.10—"DNA Microarray Preparation by Light-Controlled In Situ Synthesis"). Unless otherwise indicated, the same coupling methodology is used in subsequent steps to extend and modify all oligonucleotide chains constituting the array.

Figure 7D:
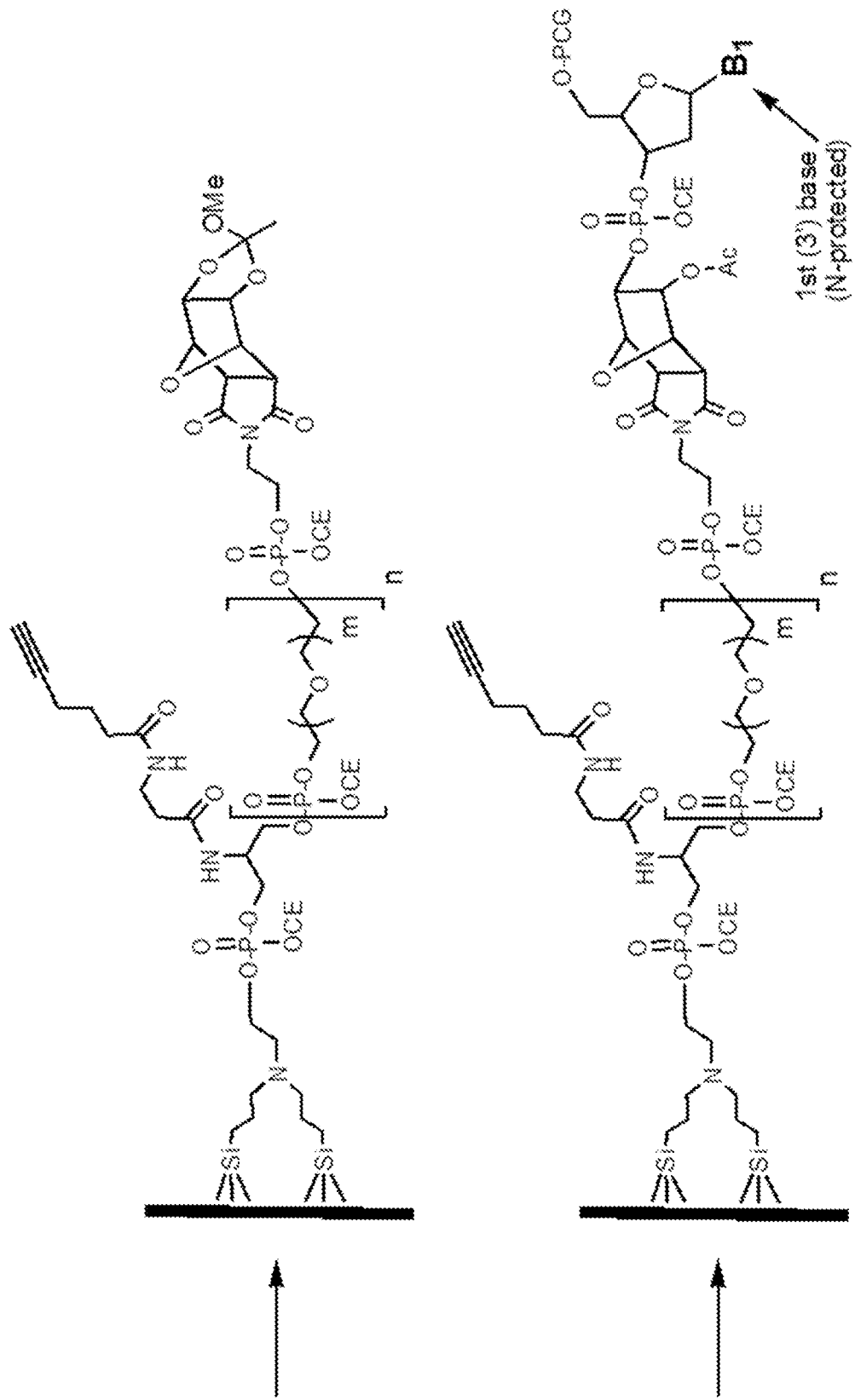
FIG. 7D shows an exemplary step of addition of a universal cleavable linker with light-directed synthesis.
Figure 7E:
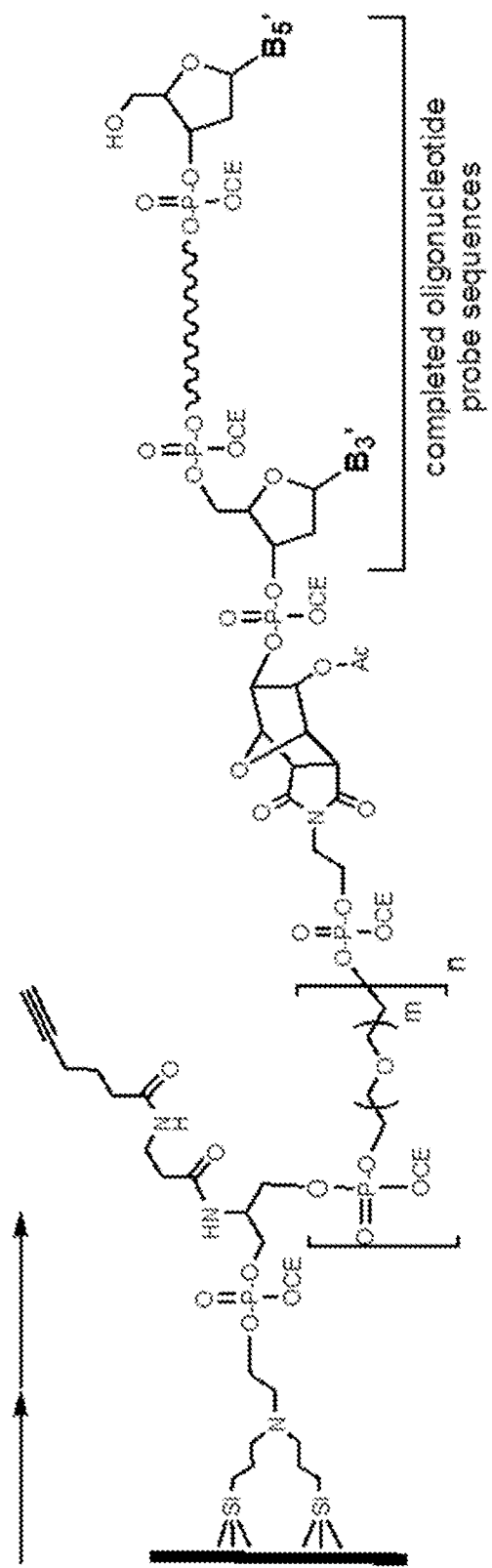
FIG. 7E shows an exemplary step of continuing photolithographic synthesis to complete the array of oligonucleotide sequences.

Light-directed synthesis protocols are then used to add a universal cleavable linker (e.g., Universal Phosphoramidite, AM Chemicals, P/N 02120) (see, e.g., FIG. 7D, top), and then a 5'-PPG-protected nucleotide corresponding to the first nucleotide of the probe sequences to be synthesized (see, e.g., FIG. 7D, bottom). This pair of steps is repeated four times, each time using a unique photolithographic mask to attach the four nucleotides A, G, C and T, through the universal linker, to regions of the substrate that have been designated for sequences starting with that base at the 3'-position. Photolithographic synthesis is continued to complete the array of oligonucleotide sequences (see, e.g., FIG. 7E—note all sequences are depicted generically).

Figure 7F:
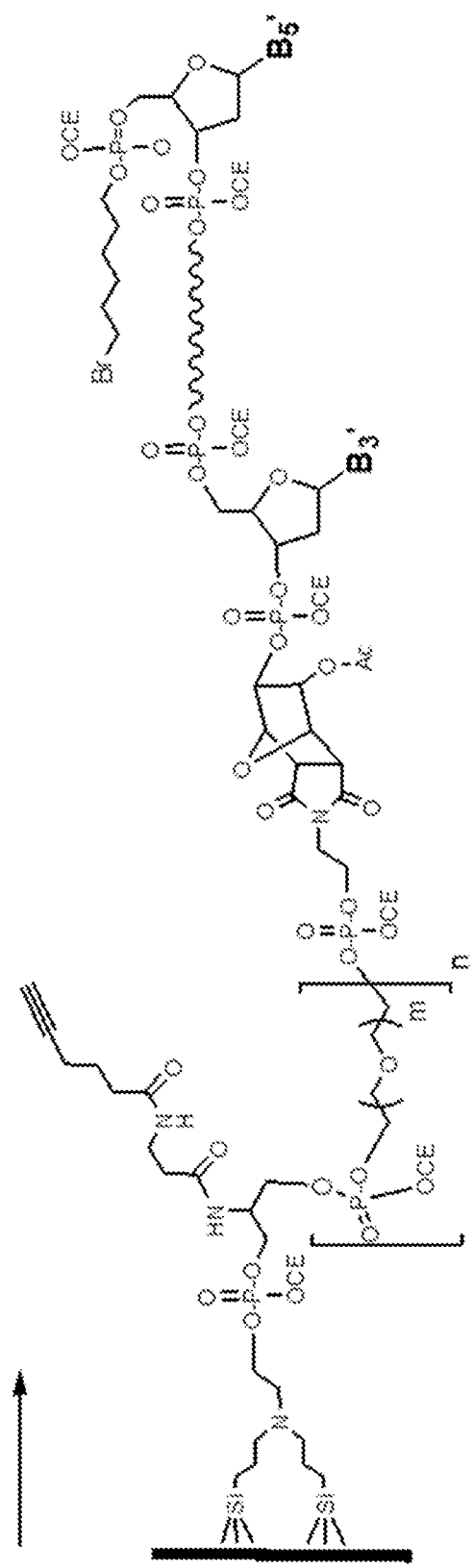
FIG. 7F shows an exemplary step of addition of 6-bromohexyl phosphoramidite to the oligonucleotide sequences.
Figure 7G:
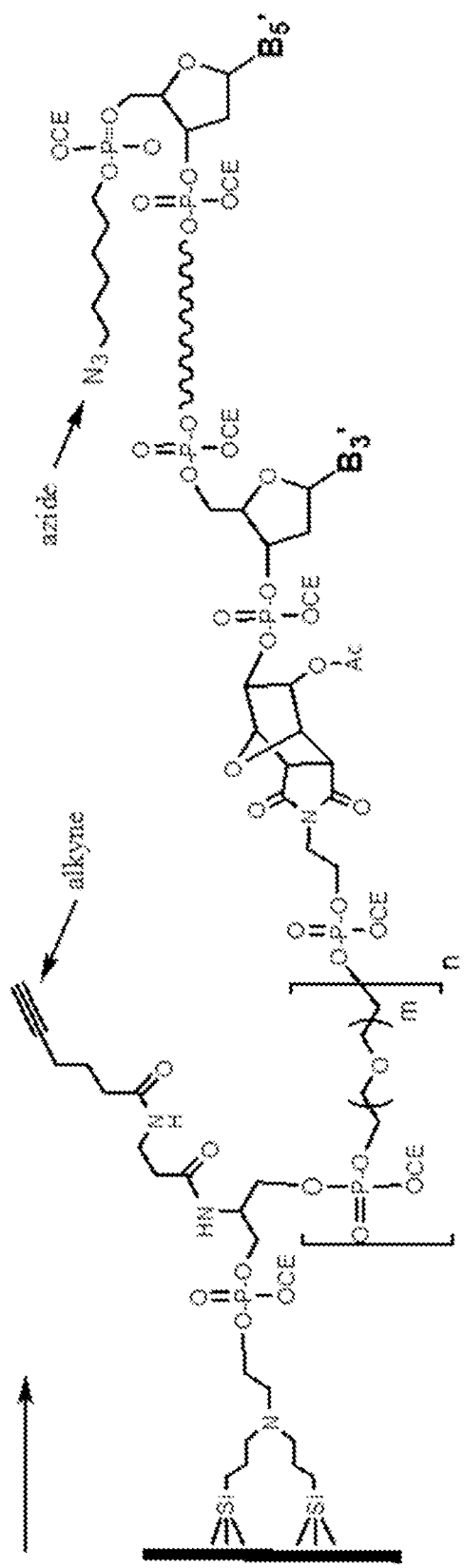
FIG. 7G shows an exemplary step of replacing bromine with an azido group by treatment with sodium azide in dimethylformamide.

After the probe sequences in the array are completed, and 5'-end deprotected, a 6-bromohexyl phosphoramidite (e.g., Glen Research, P/N 10-1992) is added to the array, on the 5' terminus of all of the sequences (see, e.g., FIG. 7F). The bromine is then replaced with an azido group by treatment of the array with sodium azide in dimethylformamide (see, e.g., FIG. 7G).

Figure 7H:
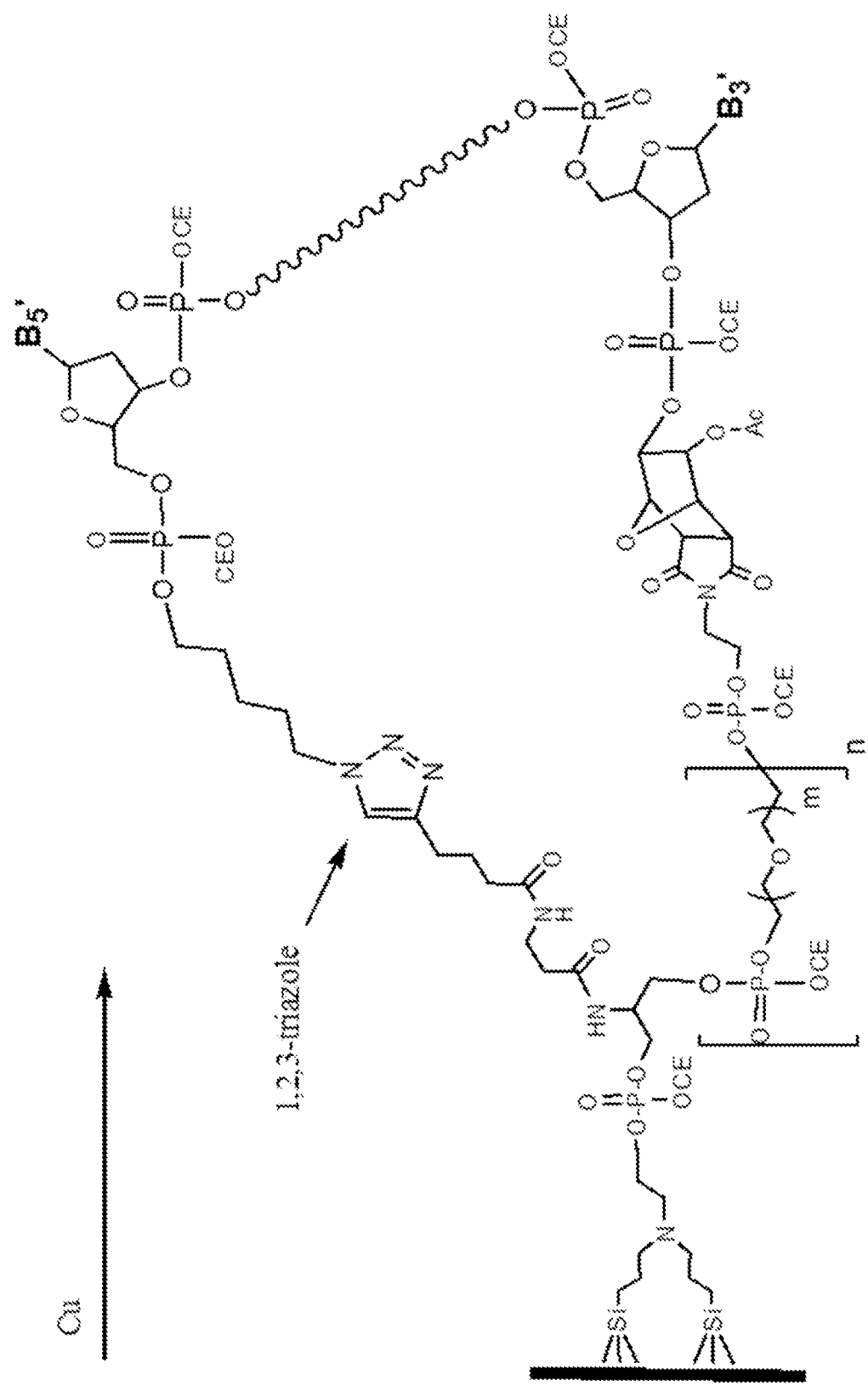
FIG. 7H shows an exemplary step of performing a Huisgen ("click") reaction with the 5'-azido group and the alkyne moieties close to the surface of the substrate.

The Huisgen ("click") reaction is then performed, in which the 5'-azido group reacts with the alkyne moieties close to the surface of the substrate (see, e.g., *JACS,* 2007, 129(21), 6859—"Template-Directed Oligonucleotide Strand Ligation, Covalent Intramolecular DNA Circularization and Catenation Using Click Chemistry"). This cycloaddition reaction is catalyzed by the addition of an aqueous solution of Cu[III] sulfate, sodium ascorbate and a ligand such as tris-triazolylamine. Optionally, the solution is de-oxygenated prior to addition. This results in formation of a covalent link in the form of a 1,2,3-triazole, between the 5'-end of the oligonucleotide (see, e.g., FIG. 7H). For simplicity, the "click" reaction is drawn as taking place between an azide and alkyne within the same oligonucleotide molecule. However it is just as likely, and of no consequence, that this reaction may also occur between the functional groups on two different, but neighboring, oligonucleotides.

Figure 7I:
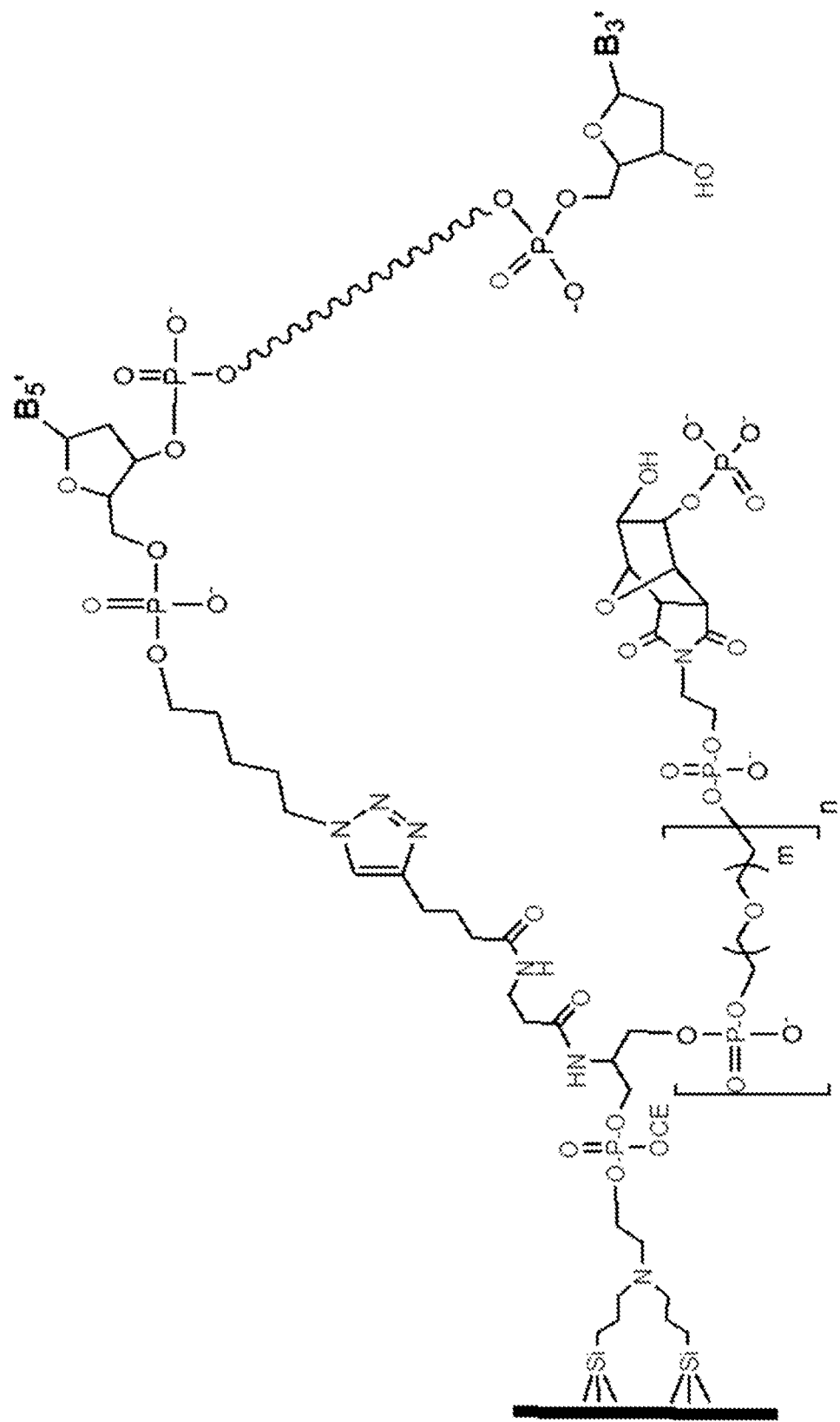
FIG. 7I shows an exemplary step of removing the acyl protecting groups from the bases of the oligonucleotide sequences and cleaving the universal linker at the 3'-end.

The entire array substrate is then treated with $NH_4OH$, $CH_3NH_2$, $NH_2CH_2CH_2NH_2$, or mixtures thereof. This removes the acyl protecting groups from the bases of the oligonucleotide sequences, and also cleaves the universal linker at the 3'-end, releasing them with free 3'-hydroxyl termini while they remain covalently bound to the support by the 5'-triazole linkage (see, e.g., FIG. 7I).

EXAMPLE 2—TESTING INVERSION EFFICIENCY

An oligonucleotide probe array is prepared as described in Example 1. Prior to inversion, sequences are attached to the substrate at the 3'-end, so they cannot serve as initiation sites for DNA polymerase, as the 3'-hydroxyl group is blocked. Once inverted, the 3'-hydroxyl groups of the sequences on the array are exposed and competent as initiation sites for DNA polymerase. Thus, probe inversion is verified simply by hybridizing sequences on the array with complementary oligonucleotide sequences having a 3' overhang. DNA polymerase is then added to the array, along with fluorescently labeled deoxynucleoside triphosphates. This results in extension of the hybridized probe sequences with one or more fluorescent nucleotides, which can be readily detected by imaging the array with a fluorescence microscope.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
   (a) providing a substrate;
   (b) coupling a branched linker to said substrate, wherein said branched linker comprises (i) a first branch comprising a post-synthesis reactive group and (ii) a second branch;
   (c) coupling a cleavable linker to said second branch;
   (d) synthesizing an oligonucleotide on said cleavable linker in 3' to 5' orientation, said oligonucleotide comprising (i) a 3' end coupled to said second branch via said cleavable linker and (ii) a 5' end coupled to a first OH group;
   (e) reacting said first OH group to provide a circularization group coupled to said 5' end of said oligonucleotide;
   (f) circularizing said oligonucleotide by reacting said circularization group with said post-synthesis reactive group, thereby coupling said 5' end of said oligonucleotide to said first branch; and
   (g) cleaving said cleavable linker, thereby de-coupling said 3' end of said oligonucleotide from said second branch,
   wherein said circularization group comprises an azido group and said post-synthesis reactive group comprises an alkyne, wherein said branched linker is coupled to said substrate via a first reagent of

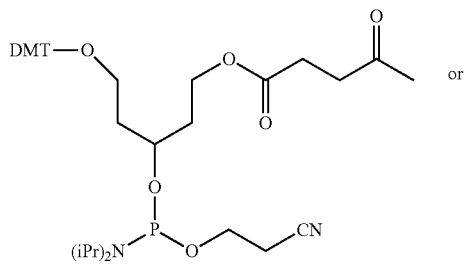

or

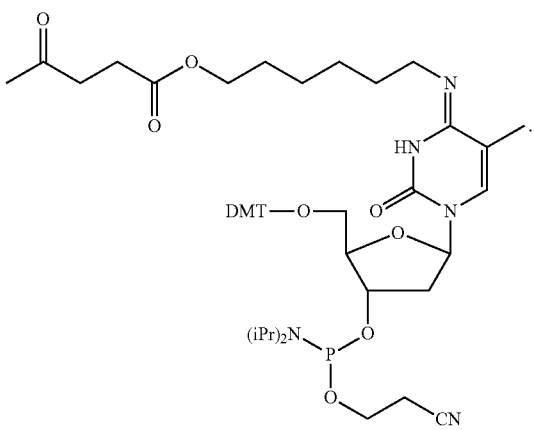

2. The method of claim 1, wherein said branched linker is coupled to said substrate via a second OH group bound to said substrate.

3. The method of claim 1, wherein said cleavable linker is coupled to said substrate via a second reagent of

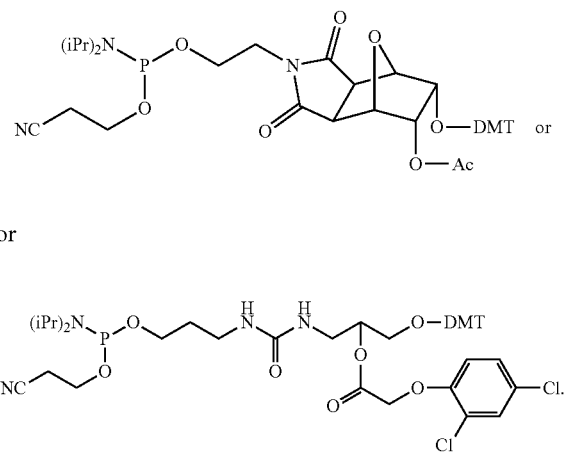

or

4. The method of claim 1, wherein said circularizing is conducted using Huisgen "click" chemistry.

5. The method of claim 1, wherein said cleaving comprises deprotection with $NH_4OH$.

6. The method of claim 1, wherein said synthesizing comprises photolithography.

7. A method, comprising:
   (a) providing a substrate comprising a plurality of sites;
   (b) coupling a branched linker to each of said plurality sites, wherein said branched linker comprises (i) a first branch comprising a post-synthesis reactive group and (ii) a second branch;
   (c) coupling a cleavable linker to said second branch of said branched linker on each of said sites;
   (d) synthesizing oligonucleotide probes in 3' to 5' orientation on said cleavable linker on each of said sites, thereby producing a (i) a full-length oligonucleotide coupled at a first 3' end to said cleavable linker of a first site and coupled at a first 5' end to a first OH group, wherein said full-length oligonucleotide comprises a target number of nucleotides, and (ii) a truncated oligonucleotide coupled at a second 3' end to said cleavable linker of a second site and lacking a second OH group at a second 5' end, wherein said truncated oligonucleotide comprises fewer than said target number of nucleotides, and;
   (e) reacting said first OH group coupled to said first 5' end of said full-length oligonucleotide to provide a circularization group coupled to said first 5' end of said full-length oligonucleotide;
   (f) circularizing said full-length oligonucleotide by reacting said circularization group with said post-synthesis reactive group of said branched linker of said first site, thereby coupling said first 5' end of said full-length oligonucleotide to said first branch of said branched linker of said first site; and
   (g) cleaving said cleavable linker of each of said plurality sites, thereby (i) de-coupling said first 3' end of said full-length oligonucleotide from said second branch of said branched linker of said first site, and (ii) releasing said truncated oligonucleotide from said second site;
   wherein said circularization group comprises an azido group and said prost-synthesis reactive group comprises an alkyne, wherein said branched linker is coupled to said substrate via a first reagent of

11

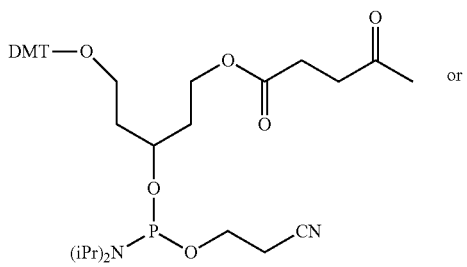

or

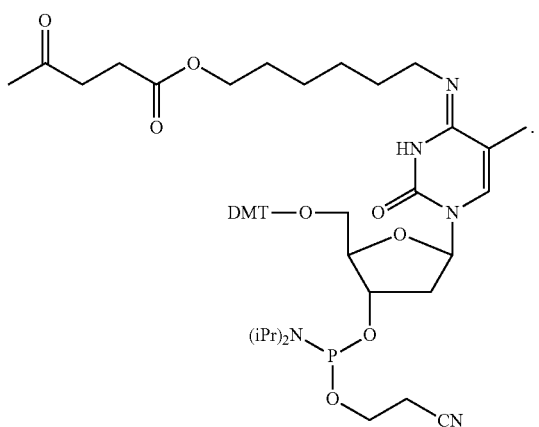

8. The method of claim 7, wherein said branched linker is coupled to said substrate via a third OH group bound to said substrate.

9. The method of claim 7, wherein said cleavable linker is coupled to said substrate via a second reagent of

12

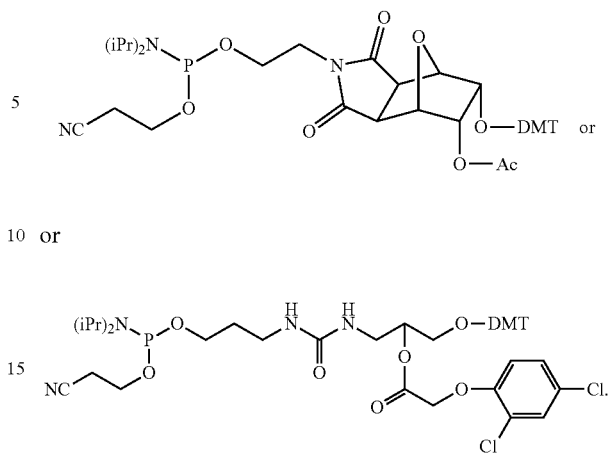

or

10. The method of claim 7, wherein said circularizing is conducted using Huisgen "click" chemistry.

11. The method of claim 7, wherein said cleaving comprises deprotection with NH₄OH.

12. The method of claim 7, wherein said synthesizing comprises photolithography.

13. The method of claim 7, wherein said cleaving releases at least 50% of oligonucleotides that comprise fewer than said target number of nucleotides from said plurality of sites.

14. The method of claim 7, wherein said cleaving releases at least 70% of oligonucleotides that comprise fewer than said target number of nucleotides from said plurality of sites.

15. The method of claim 7, wherein said cleaving releases at least 90% of oligonucleotides that comprise fewer than said target number of nucleotides from said plurality of sites.

* * * * *